United States Patent [19]

Nagata et al.

[11] Patent Number: 4,555,578
[45] Date of Patent: Nov. 26, 1985

[54] MERCAPTOTETRAZOLYLALKANOHYDROXAMIC ACIDS, SALTS AND ESTER THEREOF

[75] Inventors: Wataru Nagata, Hyogo; Tsutomu Aoki, Osaka, both of Japan

[73] Assignee: Shionogi & Co., Ltd., Osaka, Japan

[21] Appl. No.: 493,573

[22] Filed: May 11, 1983

[30] Foreign Application Priority Data

May 13, 1982 [JP] Japan ................................ 57-81128

[51] Int. Cl.$^4$ .......................................... C07D 257/04
[52] U.S. Cl. .................................................. 548/251
[58] Field of Search ....................................... 548/251

[56] References Cited

FOREIGN PATENT DOCUMENTS 0122362 9/1981 Japan ................................ 548/251
2009161 6/1979 United Kingdom .

Primary Examiner—Richard L. Raymond
Assistant Examiner—David B. Springer

Attorney, Agent, or Firm—Birch, Stewart, Kolasch & Birch

[57] ABSTRACT

5-Mercapto-1H-tetrazole-1-alkanohydroxamic acid, its salts and its esters having the following formula:

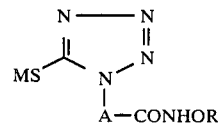

wherein
A is an alkylene group;
M is a hydrogen or light metal atom; and
R is a hydrogen atom, an alkyl group or a hydroxy-protecting group, and its preparation are disclosed. The compounds are useful as medicines and intermediates.

15 Claims, No Drawings

MERCAPTOTETRAZOLYLALKANOHYDROX-AMIC ACIDS, SALTS AND ESTER THEREOF

This invention relates to a tetrazolealkanohydroxamic acid derivative represented by the following formula:

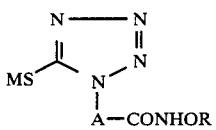

wherein
A is an alkylene group;
M is a hydrogen or light metal atom; and
R is a hydrogen atom, an alkyl group or a hydroxy-protecting group.

In the above formula, A is a straight or branched alkylene group, e.g., 1 to 3C alkylene group; M is a hydrogen atom or light metal atom, e.g., lithium, sodium, potassium, calcium, aluminum, etc.; R is a hydrogen atom, lower alkyl group, e.g. 1 to 5C alkyl, or hydroxy-protecting group, e.g., 1 to 6C alkanoyl, 4 to 7C tertiary alkyl, monocyclic aralkyl or aryl optionally substituted by e.g., 1 to 3C alkyl or alkoxy, nitro, halogen, phenyl or the like.

The tetrazolealkanohydroxamic acid derivatives are useful as additives to synthetic resins and as starting materials for highly effective medicines, e.g., cephalosporins.

The compounds of this invention can be synthesized according to the reactions of the following scheme using a conventional method in the art.

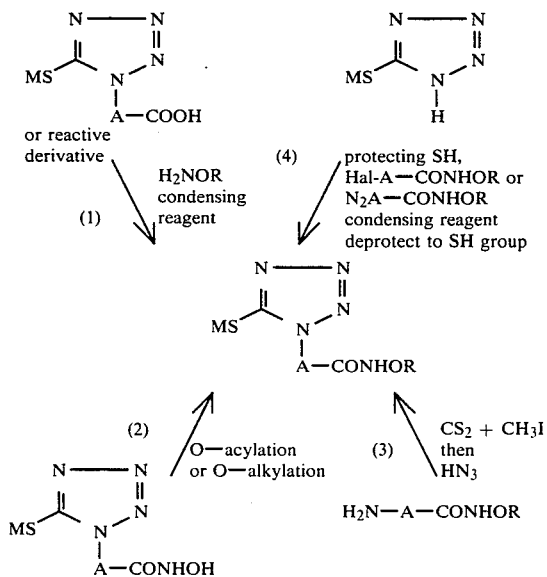

1. According to one of the synthetic methods, 5-mercapto-1H-tetrazole-1-alkanoic acid is dissolved in a solvent and mixed with an oxyamine compound H$_2$NOR in the presence of a condensing reagent, e.g., N,N'-dicyclohexylcarbodiimide, 2-ethoxy-1-ethyl-1,2-dihydroquinoline, N,N'-carbonyldimidazole, etc., in the presence of an aromatic base at a temperature between −50° C. and 100° C. for a time between 10 minutes and 10 hours.

Similarly, a reactive ester can be used instead of the free acid, for example, an enol ester, e.g., vinyl ester, isopropenyl ester, etc., aryl ester, e.g., phenyl ester, halophenyl ester, nitrophenyl ester, heterocyclic ester, e.g., pyridyl ester, benzotriazolyl ester, an ester with an N-hydroxy compound, e.g., N-hydroxysuccinimide, N-hydroxy-phthalimide, or a thiol ester, e.g., methyl thiol ester, tetrazolylthiol ester, or the like of the tetrazole-1-alkanoic acid.

Further, a halide, symmetric anhydride or mixed anhydride with a carbonic acid, sulfuric acid, phosphoric acid, carboxylic acid, sulfonic acid or the like, can also be used (if required the mercapto group may be protected in a conventional manner), in the presence of an acid scavenger, e.g., an inorganic base, tertiary amine, aromatic base, oxirane, adsorbent or the like as the condensing reagent in a solvent at a temperature preferably between −50° C. and 30° C. for, e.g., 10 minutes and 10 hours.

Equivalent methods include the following:

2. When R is hydrogen, the mercapto-1H-tetrazole-1-alkanohydroxamic acid is acylated or alkylated in a conventional manner to form the corresponding O-acylated or O-alkylated material. In the alkylation, the mercapto group is preferably protected and later deprotected.

3. An aminoalkanohydroxamic acid derivative may be treated with carbon disulfide and methyl iodide in a basic medium and then with hydrogen azide at, e.g., a temperature between room temperature and 100° C. according to a conventional manner.

4. 5-Mercapto-1H-tetrazole protected at its mercapto group in a form of a thiol ester or thio ether is treated with a haloalkanooxamate or diazoalkanooxamate in the presence of a condensing reagent, e.g., alkali metal hydride or alkoxide, trialkylamine, aromatic base, at a temperature between, e.g., −20° C. and 50° C. The mercapto protecting group is then removed in a conventional way.

The reactions referred to above are generally done at a temperature between −30° C. and 100° C., especially −20° C. and 50° C. for a time between 10 minutes and 10 hours in a solvent, if required under anhydrous condition, according to a conventional method, e.g., anhydrous or inert gas protection of the reaction medium, stirring, etc. The solvent for the reaction may be an industrial solvent belonging to the hydrocarbon (e.g., pentane, hexane, octane, benzene, toluene, xylene), halohydrocarbon (dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethyl sulfoxide, thiane-1,1-dioxide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water or the like or a mixture of more than two of the above industrial solvents, when appropriate for the reaction to be used.

The product of the above reactions can be isolated by removing unreacted starting materials, by-products, solvents or the like by extraction, evaporation, washing, concentration, precipitation, filtration, drying or the like conventional method and then purified by e.g., adsorption, elution, distillation, precipitation, separating out, chromatography or the like conventional work up procedure.

Specific compounds according to this invention, include the compound (I) wherein M=H, A=CH$_2$, R=H;
M=Na, A=CH$_2$, R=H;
M=K, A=CH$_2$, R=H;
M=H, A=CH$_2$, R=CH$_3$;
M=Na, A=CH$_2$, R=CH$_3$;
M=K, A=CH$_2$, R=CH$_3$;
M=H, A=CH$_2$, R=C$_2$H$_5$;
M=Na, A=CH$_2$, R=C$_2$H$_5$;
M=H, A=CH$_2$, R=CH(CH$_3$)$_2$;
M=Na, A=CH$_2$, R=CH(CH$_3$)$_2$;
M=H, A=CH$_2$, R=CH$_2$C$_6$H$_4$OCH$_3$-p;
M=Na, A=CH$_2$, R=CH$_2$C$_6$H$_4$OCH$_3$-p;
M=H, A=CH(CH$_3$), R=H;
M=H, A=CH$_2$CH$_2$, R=CH$_3$;
M=Na, A=CH$_2$CH$_2$, R=CH$_3$;
M=K, A=CH$_2$CH$_2$, R=CH$_3$; or
M=H, A=C(CH$_3$)$_2$, R=CH$_3$;

The following examples are given to illustrate the embodiments of this invention. The abbreviations used are those conventional in the art.

EXAMPLE 1

α-(5-Mercapto-1H-tetrazol-1-yl)acetohydroxamic acid methyl ester

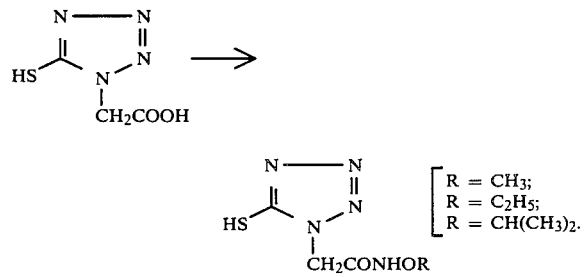

(Free acid and N,N'-carbonyldiimidazole)

To an ice cold and stirred solution of 5-mercapto-1H-tetrazole-1-acetic acid (9.6 g) in N,N-dimethylformamide (60 ml) is added N,N'-carbonyldiimidazole (11.6 g), and the mixture is stirred at 0° C. for 1 hour. To this mixture is added a solution of methoxyamine hydrochloride (11.6 g) in a mixture of N,N-dimethylformamide (45 ml) and 4.6 N-sodium methoxide methanol solution (28.5 ml) and the whole mixture is stirred under ice cooling for 1 hour. The reaction mixture is poured onto ice water and extracted with a mixture of ethyl acetate and methyl ethyl ketone (2:1). The extract solution is washed with water, dried and concentrated in vacuum. The residue is crystallized from a mixture of acetone and ether to give 5-mercapto-1H-tetrazole-1-acetohydroxamic acid methyl ester (7.73 g). mp. 175°–176° C. (decomp.).

IR (Nujol) ν: 3120, 1670 cm$^{-1}$.

NMR (CD$_3$COCD$_3$) δ: 3.77 (s, 3H), 5.08 (brs, 2H).

In a manner similar to above, but substituting methoxyamine hydrochloride with the equivalent molar equivalent of ethoxyamine acetate or isopropoxyamine sulfate, the corresponding ethyl ester or isopropyl ester of the hydroxamic acid can be prepared.

Ethyl ester NMR (CDCl$_3$+CD$_3$OD) δ: 1.13 (t, J=6 Hz, 3H), 3.88 (q, J=6 Hz, 2H), 5.08 (s, 2H).

Isopropyl ester NMR (CDCl$_3$+CD$_3$OD) δ: 1.20 (d, J=7 Hz, 6H), 4.02 (septet, J=7 Hz, 1H), 5.10 (s, 2H).

(Free acid and N,N'-dicyclohexylcarbodiimide)

To an ice cold and stirred solution of 5-mercapto-1H-tetrazole-1-acetic acid (320 mg) in methanol (3 ml) are added triethylamine (0.33 ml) and N,N'-dicyclohexylcarbodiimide (495 mg), and th mixture is stirred for 7 hours. To this solution is added a solution of methoxyamine hydrochloride (33.4 mg) and triethylamine (56 μl) in methanol (0.3 ml). After the addition of a further amount of N,N'-dicyclohexylcarbodiimide (124 mg), the mixture is left stand at room temperature overnight. The reaction mixture is concentrated under reduced pressure to about 1 ml and then diluted with ethyl acetate (8 ml) and 5% sodium hydrogen carbonate (7 ml). After the separated solid (461 mg) is removed by filtration, the filtrate is saturated with sodium chloride and diluted with ethyl acetate-methyl ethyl ketone mixture (1:1). The mixture is acidified to pH 1 with hydrochloric acid and extracted with ethyl acetate. The extract is dried over magnesium sulfate and concentrated under reduced pressure to give 5-mercapto-1H-tetrazole-1-acetohydroxamic acid methyl ester (375 mg), identical with the product prepared with N,N'-carbonyldiimidazole.

(Acid chloride)

To an ice cold solution of 5-mercapto-1H-tetrazole-1-acetic acid (160 mg) in acetonitrile (3.2 ml) are added tri-n-butylamine (476 μl) and phosphorus oxychloride (183 μl). After 80 minutes' stirring, a solution of methoxyamine hydrochloride (167 mg) and tri-n-butylamine (476 μl) in hexamethylphosphorotriamide is added to the above solution. After another 1 hour's stirring at 0° C., the mixture is extracted with 5% aqueous sodium hydrogen carbonate (40 ml). The extract solution is washed with ethyl acetate, acidified with concentrated hydrochloric acid to pH 2.5, saturated with sodium chloride and extracted with methyl ethyl ketone. The extract is dried over magnesium sulfate and concentrated to give 5-mercapto-1H-tetrazole-1-acetohydroxamic acid methyl ester (134 mg). mp. 165°–167° C. (decomp.).

In a manner similar to above, but substituting phosphorus oxychloride with triphenylphosphine (1.2 molar equivalents) and carbon tetrachloride (320 mg) and the acid chloride is formed in the presence of free methoxyamine in N,N-dimethylformamide (2.5 ml), the same product can be obtained in high yield.

(Mixed anhydride)

To a solution cooled at −28° C. to −35° C. of 5-mercapto-1H-tetrazole-1-acetic acid (0.8 g) in tetrahydrofuran (40 ml) are added N-methylmorpholine (1.26 ml) and ethyl chloroformate (0.62 ml). After stirring for 1 hour, a solution of methoxyamine hydrochloride (0.34 g) and N-methylmorpholine (0.71 ml) in tetrahydrofuran (11 ml) is added to the mixture at −50° C. After 2 hours' stirring at about −30° C., the mixture is concentrated under reduced pressure, and the resultant mixture is diluted with water (50 ml) and ethyl acetate (50 ml). The mixture is acidified to pH 2 with hydrochloric acid and extracted with ethyl acetate. The extract solution is dried over magnesium sulfate and concentrated to give 5-mercapto-1H-tetrazole-1-acetohydroxamic acid methyl ester. mp. 165°–167° C. (decomp.).

In a manner similar to above, but substituting ethyl chloroformate with diphenyl chlorophosphonate, N-methylmorpholine with tri-n-butylamine (2 molar equivalents) and tetrahydrofuran with acetonitrile, the same product can be prepared.

EXAMPLE 2

(1) α-(5-mercapto-1H-tetrazol-1-yl)acetohydroxamic acid p-methoxybenzyl ester

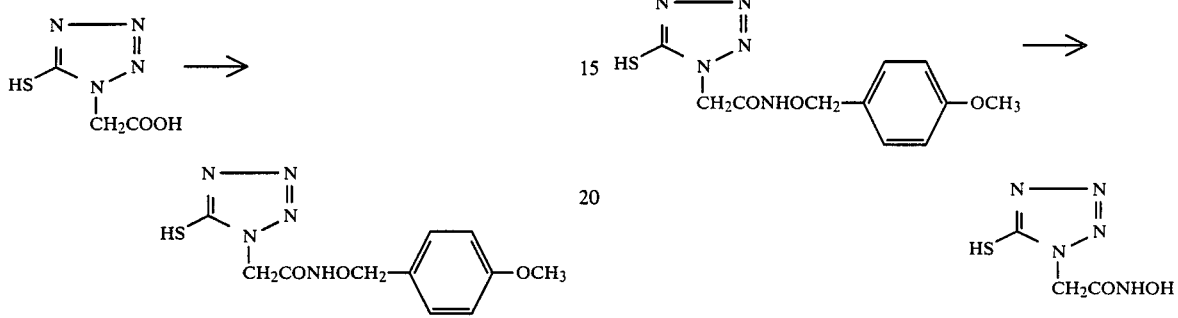

To an ice cold solution of 5-mercapto-1H-tetrazole-1-acetic acid (4.4 g) in N,N-dimethylformamide (40 ml) is added N,N'-carbonyldiimidazole (4.86 g), and the mixture is stirred under nitrogen for 1 hour. To this solution is added a solution of p-methoxybenzyloxyamine (7.9 g) in N,N-dimethylformamide (10 ml), and the mixture is stirred under ice cooling for 45 minutes. The reaction mixture is poured onto ice water containing hydrochloric acid and extracted with ethyl acetate. The extract solution is washed with water, dried and concentrated under reduced pressure. The residue is crystallized from a mixture of acetone and ether to give the title compound (7.3 g). mp. 167°–168° C.

IR (Nujol) $\nu$: 3060, 1630, 1605 cm$^{-1}$.

NMR (CD$_3$COCD$_3$) δ: 3.80 (s, 3H), 4.90 (s, 2H), 5.06 (brs, 2H), 6.97d+7.46d (ABq, J=9 Hz, 4H).

(p-methoxybenzyloxyamine, one of the starting materials)

To a solution of N-hydroxyphthalimide (11.1 g) and p-methoxybenzyl bromide (13.7 ml) in N,N-dimethylformamide (100 ml) is added triethylamine (6.8 g), and the mixture is stirred at room temperature for 1 hour and at 60° to 70° C. for 1 hour. The reaction mixture is poured into ice water and extracted with ethyl acetate. The extract solution is washed with diluted hydrochloric acid and water, dried and concentrated under reduced pressure. The residue is crystallized from methanol to give N-p-methoxybenzyloxyphthalimide (17 g). mp. 139°–141° C.

IR (Nujol) $\nu$: 1720 cm$^{-1}$.

NMR (CDCl$_3$) δ: 3.80 (s, 3H), 5.16 (s, 2H), 6.96d+7.55d (ABq, J=9 Hz, 4H), 7.83 (s, 4H).

To a solution of N-p-methoxybenzyloxyphthalimide (10.55 g) prepared as above in a mixture of N,N-dimethylformamide (70 ml) and methanol (20 ml) is added hydrazine hydrate (3.7 ml) with stirring at room temperature, and the mixture is stirred for 1 hour at the same temperature. Then, the mixture is mixed with 2N-hydrochloric acid (61.5 ml) and stirred for 20 minutes at the same temperature. The reaction mixture is diluted with water (30 ml) and separated crystals are removed by filtration. The filtrate is washed with ethyl acetate, made alkaline with potassium carbonate and extracted with ethyl acetate. The extract solution is washed with water, dried and concentrated under reduced pressure. The residue is the objective p-methoxybenzyloxyamine (6.09 g).

IR (film) $\nu$: 3400, 3280, 1660, 1600, 1580 cm$^{-1}$.

NMR (CDCl$_3$) δ: 3.78 (s, 3H), 4.63 (s, 2H), 5.33 (brs, 2H), 6.91d+7.33d (ABq, J=9 Hz, 4H).

(2) α-(5-Mercapto-1H-tetrazol-1-yl)acetohydroxamic acid

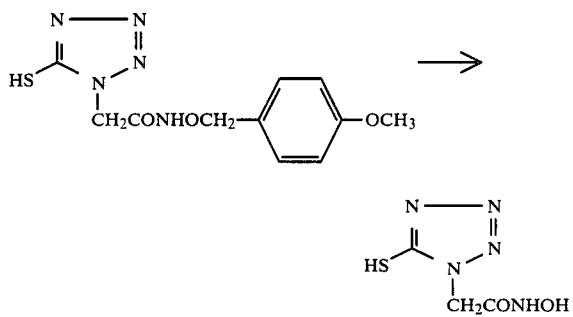

To a mixed solvent of trifluoroacetic acid (15 ml) and anisole (15 ml) is added 5-mercapto-1H-tetrazole-1-acetohydroxamic acid p-methoxybenzyl ester (3 g), and the mixture is stirred at room temperature for 2 hours under nitrogen gas. The reaction mixture is concentrated under reduced pressure, and the resultant material is dissolved in water and passed through a column of synthetic resin adsorbent (Diaion HP-20 distributed by Mitsubishi Chemical K.K.) (95 ml). The resin is washed with water. The fractions containing the main product are combined and concentrated under reduced pressure. The resultant solid is crystallized from a mixture of ether and hexane to give the title compound (1.83 g). mp. 105°–107° C.

IR (Nujol) $\nu$: 3100, 1655 cm$^{-1}$.

NMR (CD$_3$COCD$_3$) δ: 5.08 (brs, 2H).

EXAMPLE 3

Sodium 1-N-methoxycarbamoylmethyl-1H-tetrazol-5-ylmercaptide

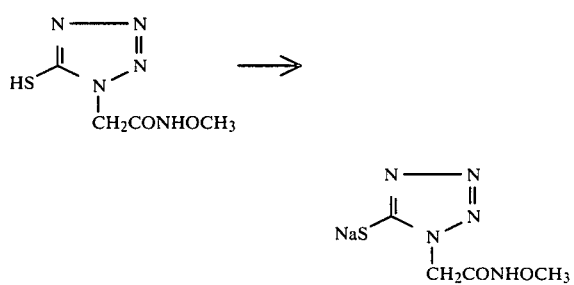

A solution of 5-mercapto-1H-tetrazole-1-acetohydroxamic acid methyl ester (945 mg) and sodium hydrogen carbonate (420 mg) in water (30 ml) is frozen and lyophilized overnight to give a hygroscopic sodium salt of 5-mercapto-1H-tetrazole-1-acetohydroxamic acid methyl ester as a solid.

IR (Nujol) $\nu$: 3300br, 1670br cm$^{-1}$.

NMR (D$_2$O) δ: 4.19 (s, 3H), 5.47 (s, 2H).

EXAMPLE 4

β-(5-Mercapto-1H-tetrazol-1-yl)propiohydroxamic acid methyl ester

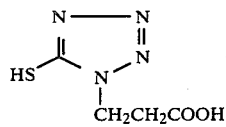 

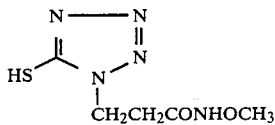

To an ice cold and stirred solution of 5-mercapto-1H-tetrazole-1-propionic acid (1.04 g) in N,N-dimethylformamide (60 ml) is added N,N'-carbonyldiimidazole (1.16 g). After stirring for 15 minutes at 0° C., the mixture is mixed with a solution of methoxyamine hydrochloride (600 mg) and triethylamine (720 mg) in N,N-dimethylformamide (6 ml) and stirred for 1 hour at 0° C. The reaction mixture is poured into diluted hydrochloric acid and extracted with a mixture of ethyl acetate and methyl ethyl ketone (2:1). The solvent is evaporated from the extract to leave crystalline 5-mercapto-1H-tetrazole-1-propionohydroxamic acid methyl ester (1.2 g). mp. 170°–171° C. (decomp.).

NMR (CD$_3$COCD$_3$) δ: 2.77 (brs, 2H), 3.66 (s, 3H), 4.52 (t, J=7 Hz, 2H).

IR (Nujol) ν: 3110, 1645 cm$^{-1}$.

What we claim is:

1. A tetrazolylalkanohydroxamic acid or its ester represented by the following formula:

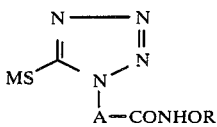

wherein A is methylene, ethylene or propylene; M is a hydrogen or light metal atom; and R is methyl, ethyl or isopropyl.

2. The compound claimed in claim 1, wherein M is hydrogen.

3. The compound claimed in claim 1, wherein M is a light metal atom.

4. The compound claimed in claim 1, wherein M is sodium or potassium.

5. The compound claimed in claim 1, wherein M is hydrogen, A is methylene and R is methyl.

6. The compound claimed in claim 1, wherein M is sodium, A is methylene and R is methyl.

7. The compound claimed in claim 1, wherein M is potassium, A is methylene and R is methyl.

8. The compound claimed in claim 1, wherein M is hydrogen, A is methylene and R is ethyl.

9. The compound claimed in claim 1, wherein M is sodium, A is methylene and R is ethyl.

10. The compound claimed in claim 1, wherein M is hydrogen, A is methylene and R is isopropyl.

11. The compound claimed in claim 1, wherein M is sodium, A is methylene and R is isopropyl.

12. The compound claimed in claim 1, wherein M is hydrogen, A is ethylene and R is methyl.

13. The compound claimed in claim 1, wherein M is sodium, A is ethylene and R is methyl.

14. The compound claimed in claim 1, wherein M is potassium, A is ethylene and R is methyl.

15. The compound claimed in claim 1, wherein M is hydrogen, A is propylene and R is methyl.

* * * * *